United States Patent [19]

Jakubowski et al.

[11] Patent Number: 4,830,657
[45] Date of Patent: May 16, 1989

[54] SYNERGISTIC ANTIMICROBIAL COMBINATION

[75] Inventors: John A. Jakubowski, Piscataway; Joseph Gyuris, Middletown, both of N.J.

[73] Assignee: Calgon Corporation, Pittsburgh, Pa.

[21] Appl. No.: 390,443

[22] Filed: Jun. 21, 1982

[51] Int. Cl.$^4$ ............................................. A01N 43/80
[52] U.S. Cl. ........................................ 71/67; 162/161; 514/327
[58] Field of Search ........................... 71/67; 162/161; 424/270; 514/327

[56] References Cited

U.S. PATENT DOCUMENTS 3,065,123  11/1962  Hinton et al. ............................. 71/67
3,877,922  4/1975  Grier et al. ............................... 71/67

FOREIGN PATENT DOCUMENTS 6071009  11/1979  Japan .

Primary Examiner—Catherine L. Mills
Attorney, Agent, or Firm—W. C. Mitchell; M. C. Sudol, Jr.

[57] ABSTRACT

Synergistic antimicrobial combination comprising 2-bromo-2-bromomethylglutaronitrile of Formula I:

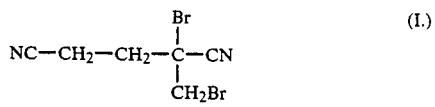

and a 1,2-benzisothiazolin-3-one of Formula II:

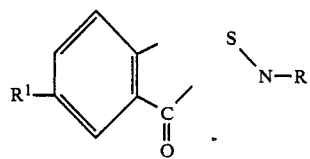

where R is hydrogen or $C_{1-4}$ alkyl; and $R^1$ is hydrogen, chloro, or methyl.

16 Claims, No Drawings

SYNERGISTIC ANTIMICROBIAL COMBINATION

BACKGROUND OF THE INVENTION

1. Field of the Invention

The present invention is concerned with the synergistic antimicrobial combination comprising (a) 2-bromo-2-bromomethylglutaronitrile and (b) a 1,2-benzisothiazolin-3-one.

The present invention is also concerned with antimicrobial compositions containing the synergistic combination as active ingredient, as well as with a method of inhibiting the growth of bacteria, yeast, fungi, and algae by contacting said bacteria, yeast, fungi, and algae with the synergistic combination of the present invention. The synergistic antimicrobial combination has a number of important industrial and agricultural applications.

As used herein, the term "antimicrobial" describes the killing of, as well as the inhibition of or control of the growth of bacteria, yeasts, fungi, and algae. A number of important industries can experience serious adverse effects from the activity of such bacteria and fungi on the raw materials which they employ, on various aspects of their manufacturing activities, or on the finished products which they produce. Such industries include the paint, wood, textile, cosmetic, leather, tobacco, fur, rope, paper, pulp, plastics, fuel, oil, rubber, and machine industries. Important applications of the synergistic antimicrobial combination of the present invention include: inhibiting the growth of bacteria in aqueous paints, adhesives, latex emulsions, and joint cements; preserving wood; preserving cutting oils; controlling slime-producing bacteria and fungi in pulp and paper mills and cooling towers; as a spray or dip treatment for textiles and leather to prevent mold growth; as a component of anti-fouling paints to prevent adherence of fouling organisms; protecting paint films, especially exterior paints, from attack by fungi which occurs during weathering of the paint film; protecting processing equipment from slime deposits during manufacture of cane and beet sugar; preventing microorganism buildup and deposits in air washer or scrubber systems and in industrial fresh water supply systems; controlling microorganism contamination and deposits in oil field drilling fluids and muds, and in secondary petroleum recovery processes; preventing bacterial and fungal growth in paper coating processes which might adversely affect the quality of the paper coating; controlling bacterial and fungal growth and deposits during the manufacture of various specialty boards, e.g., cardboard and particle board; preventing sap stain discoloration on freshly cut wood of various kinds; controlling bacterial and fungal growth in clay and pigment slurries of various types which are manufactured for later use in paper coating and paint manufacturing for example, and which are susceptible to degradation by microorganisms during storage and transport; as a hard surface disinfectant to prevent growth of bacteria and fungi on walls, floors, etc.; and in swimming pools to prevent algal growth. The control of bacteria and fungi in pulp and paper mill water systems which contain aqueous dispersions of papermaking fibers is especially important. The uncontrolled buildup of slime produced by the accumulation of bacteria and fungi causes offgrade production, decreased production due to breaks and greater cleanup frequency, increased raw material usage, and increased maintenance costs. The problem of slime deposits has been aggravated by the widespread use of closed white water systems in the paper industry.

Another important area where control of bacterial and fungal growth is vital is in clay and pigment slurries. These slurries are of various clays, e.g. kaolin, and pigments, e.g. calcium carbonate and titanium dioxide, and are manufactured usually at a location separate from the end use application, in for example, paper coating and paint manufacturing, and are then stored and held for later transport to the end use location. Because of the high quality standards for the paper and paint final products in which the slurry is used, it is essential that the clay or pigment slurry have a very low microorganism count or content so that it is usable in the paper coating or paint manufacturing.

The synergistic antimicrobial combination of the present invention may also be utilized for agricultural and animal health applications, for example in preventing or minimizing the growth of harmful bacterial, yeast, and/or fungi on plants, trees, fruit, seeds, or soil. The synergistic combination is especially useful in treating seed to prevent microorganism, particularly fungal attack. The synergistic combination is also useful in protecting animal dip compositions against the buildup of microorganisms, and for this purpose may be combined with a veterinary animal dip parasiticide and an acceptable carrier.

The synergistic combination of the present invention has been found especially useful in controlling the harmful effects of microorganisms in water or aqueous media. Systems which utilize circulating water or aqueous media become infected with microorganisms and experience substantial impairment of their efficiency when deposits of the microorganisms build up in the system. The deposits, called slimes, coat the walls of tanks and other vessels, and any machinery or processing equipment which is employed, and create blockages in pipes and valves. The slimes also create discolorations and other imperfections in any products being produced, forcing costly shutdowns. Control of microorganisms in aqueous media is particularly important where there are dispersed particles or fines in the aqueous media, e.g., dispersed cellulosic fibers and dispersed fillers and pigments in papermaking, and dispersed pigments in paint manufacture.

2. Brief Description of the Prior Art

Grier, et. al., U.S. Pat. Nos. 3,833,731 and 3,877,922; and Harmetz, et. al. U.S. Pat. No. 3,873,597 describe 2-bromo-2-bromomethylglutaronitrile and related compounds and their use as antibacterial, antifungal, and algicidal agents.

Hinton et al. U.S. Pat. No. 3.065,123 describes a process for controlling micro-organisms in water and aqueous media by the addition of certain 1:2-benzisothiazolones.

British Pat. No. 1,531,431 describes treatment with N-alkyl 1,2-benzisothiazolin (3) ones for controlling microorganisms in water-based paints and adhesives, water-oil emulsions, and metalworking fluids.

Gazzard et al. U.S. Pat. No. 3,970,755 describes biocidal compositions comprising certain quaternary ammonium compounds and 1,2-benzisothiazolin-3-ones.

German Pat. No. 2,428,334 describes a synergistic biocidal composition, especially for aqueous systems, containing isothiazolin-3-ones and 2-thiono-tetrahydro-1,3,5-thiadiazines.

Japanese Pat. No. 6071-009 describes a preservative and bacteriostatic agent containing 2-(thiocyanomethylthio)benzothiazole and 1,2-benzisothiazolin-3-one.

Japanese Pat. No. 2087-230 describes a fungicidal composition comprising alkylpoly(aminoethyl)glycine salt and 1,2-benzisothiazolin-3-one.

However, there is no suggestion in any of the above references of the synergistic antimicrobial combination of the present invention or its broad spectrum of antimicrobial activity.

DETAILED DESCRIPTION OF THE INVENTION AND PREFERRED EMBODIMENTS

In accordance with the present invention there is provided the synergistic antimicrobial combination comprising 2-bromo-2-bromomethylglutaronitrile of the formula:

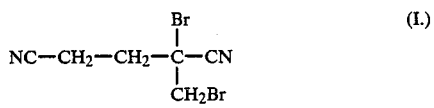

and a 1,2-benzisothiazolin-3-one of the formula:

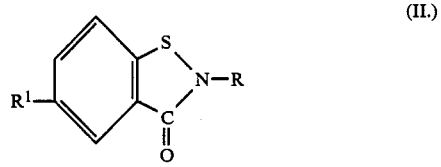

where R is hydrogen or $C_{1-4}$ alkyl; and $R^1$ is hydrogen, chloro, or methyl.

A preferred 1,2-benzisothiazolin-3-one is that where both R and $R^1$ are hydrogen and the compound is 1,2-benzisothiazolin3-one.

The benzisothiazolinones of Formula II may be used in the form of a salt with a strong inorganic or organic acid, such as hydrochloric acid, sulfuric acid, nitric acid, perchloric acid, p-toluenesulfonic acid, hydrobromic acid, chlorosulfuric acid, chloroacetic acid, oxalic acid, maleic acid, succinic acid, and the like.

The proportions of the two components of the synergistic combination are dictated by the dosage levels of each component, based on 100% active ingredient, which will be employed in each end use application. These recommended dosage levels are described in detail further below.

In accordance with the present invention there is further provided an antimicrobial composition comprising a carrier and an antimicrobially effective amount of the synergistic antimicrobial combination comprising 2-bromo-2-bromomethylglutaronitrile and a 1,2-benzisothiazolin-3-one of Formula II.

The synergistic antimicrobial combination active ingredient of the antimicrobial composition of the present invention may be used in diverse formulations: solid, including finely divided powders and granular materials; as well as liquid, such as solutions, emulsions, suspensions, concentrates, emulsifiable concentrates, slurries and the like, depending upon the application intended, and the formulation media desired. Further, when the synergistic antimicrobial combination is liquid, it may be employed neat or may be incorporated into various formulations, both solid and liquid, as an adsorbate on suitable inert carriers such as talc, clays, diatomaceous earth and the like.

Thus, it will be appreciated that the synergistic antimicrobial combination may be employed to form antimicrobial formulations containing the combination as the essential active ingredient, which formulations may also contain a variety of carrier materials adaptable to industrial and agricultural applications including finely divided dry or liquid diluents, extenders, clays, diatomaceous earth, talc and the like, or water and various organic liquids such as loweralkanols, kerosene, benzene, toluene and other petroleum distillate fractions or mixtures thereof.

The individual components of the synergistic antimicrobial combination of the present invention may be formulated into separate antimicrobial compositions for separate addition to an article or system to be treated. Such separate antimicrobial compositions may be prepared in the manner described above. For example, the 1,2-benzisothiazolin-3-ones of Formula II may be combined with ethylenediamine or propylene glycol and added to a clay slurry to which there is also added 2-bromo-2-bromomethylglutaronitrile as a dry powder.

It will be understood also that the synergistic antimicrobial combination active ingredients may be used in combination with other antimicrobial materials. For example, the combination can be combined with other fungicides and bactericides such as 2-(4'-thiazolyl)benzimidazole, sorbic acid, propionic acid, mycostatin, sodium diacetate, trichomycin, amphotericin, griseofulvin, undecylenic acid, esters of parahydroxybenzoic acid, chlorguinaldol, 5,7-dichloro-8-hydroxyquinoline, sodium-o-phenylphenate, o-phenylphenol, biphenyl chlorinated phenols, sodium benzoate in appropriate concentrations and in appropriate instances so as to combine the action of each to obtain particularly useful results. Such combinations might find particular application in the preparation of germicidal soaps, in the production of cosmetics and aqueous coatings and in combatting paper mill slime accumulations. It is quite clear also that the synergistic antimicrobial combination can be combined with other algicidal agents such as benzalkonium chlorides and other quaternary ammonium compounds to obtain formulations particularly suitable to special problems of algae control.

In accordance with the present invention there is still further provided a method of inhibiting the growth of at least one of: bacteria, yeast, fungi, and algae, comprising contacting said bacteria, yeast, fungi, or algae, with a bactericidally, fungicidally, or algicidally effective amount of the synergistic antimicrobial combination comprising 2-bromo-2-bromomethylglutaronitrile and a 1,2-benzisothiazolin-3-one of Formula II.

The antimicrobial methods of treatment of the present invention involve contacting the microorganisms involved with the synergistic antimicrobial combination. This can be accomplished either by simple addition of the two components of the combination together as a single composition, or by addition of the two components separately. Such separate co-administration can either be at the same time or at different times. The net effect will be the same: the article or system being treated will ultimately have incorporated therein or have applied thereto the desired dosage concentration of each component.

As noted above, the instant invention is based upon the discovery that the synergistic antimicrobial combination described above is effective in controlling the growth of bacteria, yeast, fungi and algae in a variety of industrial and agricultural applications. It has been found, for example, that the combination is an effective antimicrobial for the destruction or control of soil fungi and bacteria and for the protection of seeds, bulbs and plants. Also, it is an effective algicide in the treatment of pools and ponds, cooling water systems and the like. The utility of the synergistic antimicrobial combination of this invention is shown not only by its activity against bacteria and fungi responsible for stunting growth, and even destruction of many types of crop-producing plants, but also against those causing degradation and deterioration of many types of industrial products including, for example, paper, leather, textiles, aqueous systems such as adhesives, resins, drilling fluids, pigment dispersions and latex paints and oleoresinous coatings whose films are particularly vulnerable to the destructive action of fungi. The large economic losses encountered in paper-making operations caused by the accumulation of bacterial and fungal slimes in various parts of the system can be eliminated to a significant extent by use of the synergistic combination described herein.

Thus, for pulp and paper mill systems, there is provided a method of inhibiting the growth of slime-forming bacteria, fungi, and algae, usually encountered in pulp and paper mill systems, comprising incorporating into the mass of fiber and water in such a pulp and paper mill system so as to contact said bacteria, fungi, and algae, at least a bactericidally, fungicidally, and algicidally effective amount of the synergistic antimicrobial combination comprising 2-bromo-2-bromomethylglutaronitrile and a 1,2-benzisothiazolin-3-one of Formula II.

There is further provided a method of inhibiting the growth of bacteria and fungi in aqueous slurries of clays or pigments comprising incorporating into said aqueous slurry so as to contact said bacteria and fungi, at least a bactericidally and fungicidally effective amount of the synergistic antimicrobial combination comprising 2-bromo-2-bromomethylglutaronitrile and a 1,2-benzisothiazolin-3-one of Formula II.

There is still further provided a method of inhibiting the growth of bacteria, fungi, and yeast in latex paints and latex emulsions and adhesives comprising incorporating into said latex paints, emulsions, and adhesives so as to contact said bacteria, fungi, and yeast, at least a bactericidally and fungicidally effective amount of the synergistic antimicrobial combination comprising 2-bromo-2-bromomethylglutaronitrile and a 1,2-benzisothiazolin-3-one of Formula II.

There is yet futher provided a method of inhibiting the growth of bacteria, fungi, and yeast in metalworking fluids comprising incorporating into said fluids so as to contact said bacteria, fungi, and yeast, at least a bactericidally and fungicidally effective amount of the synergistic antimicrobial combination comprising 2-bromo-2-bromomethylglutaronitrile and a 1,2-benzisothiazolin-3-one of Formula II.

The antimicrobial activity of the compounds described above has been confirmed using standard laboratory techniques. They have been found effective, for example, in inhibiting bacteria including *Aerobacter aerogenes*, *Pseudomonas* species including fluorescens and aeruginosa, and *Escherichia coli*. They have been found effective also against fungi including Penicillium species, Saccharomyces species, Candida species, Fusarium species, and Cephalosporium species. Such bacteria and/or fungi commonly are found on cereal and grain products, in clay and pigment slurries, on oils, on fruits and vegetables and on cosmetics, leather, electrical insulation, textiles and numerous other materials capable of supporting their growth. Also, such bacteria and/or fungi may be found on plants, seeds, fur and wood and in soils. Further, they may be used to control overgrowth of algae such as *Chlorella sp.* including *C. pyrenoidosa*.

As noted above, it has been found that growth of various harmful fungi and bacteria existing in soil is eliminated or limited by use of formulations containing the synergistic antimicrobial combination described herein. The term "soil" as used here is intended to include all media capable of supporting growth of plants and may include humus, sand, manure, compost, artificially created plant growth solutions and the like.

The synergistic antimicrobial combination described above has activity against bacteria, yeast, fungi, and algae when employed at appropriate levels of concentration and may be used to inhibit growth of these organisms. It will be obvious to those skilled in the art that the required effective concentration will vary with particular organisms and in particular applications. In general, however, effective fungicidal, bactericidal and algicidal response is obtained when the synergistic antimicrobial combination is employed in concentrations ranging between 10 and 1000 ppm (parts per million) of 2-bromo-2-bromomethylglutaronitrile and between 3 and 300 ppm of a 1,2-benzisothiazolin-3-one of Formula II.

For latex paints, latex emulsions and adhesives, amounts of from 100 to 1000 ppm, preferably 200 to 500 ppm, of 2-bromo-2-bromomethylglutaronitrile, and of from 150 to 300 ppm, preferably 180 to 270 ppm, of a 1,2-benzisothiazolin-3-one of Formula II are added during manufacture of the paint, emulsion, or adhesive in order to protect the system during in-can storage against bacteria, fungi, and yeasts.

For aqueous clay and pigment slurries, amounts of from 10 to 250 ppm, preferably 75 to 200 ppm of 2-bromo-2-bromomethylglutaronitrile, and 3 to 75 ppm, preferably 22 to 60 ppm, of a 1,2-benzisothiazolin-3-one of Formula II are added to said slurries in order to inhibit the growth of bacteria and fungi in said slurries; and for pulp and paper mills, amounts of from 50 to 250 ppm, preferably 100 to 200 ppm. of 2-bromo-2-bromomethylglutaronitrile, and 15 to 75 ppm, preferably 30 to 60 ppm, of a 1,2-benzisothiazolin-3-one of Formula II, are added to the pulp suspension in a paper mill in order to inhibit the growth of slime-forming bacteria, fungi, yeasts and algae.

For metalworking fluids, i.e. cutting oils, amounts of from 100 to 1000 ppm, preferably 250 to 750 ppm, of 2-bromo-2-bromomethylglutaronitrile, and 150 to 300 ppm, preferably 180 to 270 ppm, of a 1,2-benzisothiazolin-3-one of Formula II, are added in order to inhibit the growth of bacteria, fungi, and yeasts during the use cycle of an oil-water lubricant for metal surfaces.

For other applications of the type described above, amounts of from 0.005 to 0.05% by weight, based on weight of the substrate being treated, of the synergistic antimicrobial combination of the present invention is incorporated into, sprayed onto, used to dip, or otherwise applied to the substrate to be treated in order to prevent growth of bacteria, fungi, yeasts, and algae.

Following is a table summarizing the dosage ranges for the components of the synergistic antimicrobial combination of the present invention in various types of end uses:

| Application | Concentration (ppm) | |
|---|---|---|
| | 2-Br—2-BG* | 1,2-BI—3-O** |
| Metal Working Fluids | 100–1000 | 150–300 |
| Latex Paints | 100–1000 | 150–300 |
| Latex Emulsions | 100–1000 | 150–300 |
| Clay & Pigment Slurries | 10–250 | 3–75 |
| Adhesives | 100–1000 | 150–300 |
| Paper Coatings | 50–250 | 15–75 |

*2-Br—2-BG = 2-bromo-2-bromomethylglutaronitrile
**1,2-BI—3-O = 1,2-benzisothiazolin-3-one Of course, the precise dosages of the components which will be employed depends upon a number of factors. First, the dosage is indicated in parts per million (ppm), which refers to the concentration of the active ingredient in the environment being treated, for example, the concentration of 2-bromo-2-bromomethylglutaronitrile in a clay slurry. This concentration is based on 100% active ingredient for convenience in evaluating and comparing test data. In actual practice, however, various percentages of active ingredient may actually be used, with the balance of the composition being added comprising conventional excipients such as dispersants, stabilizers, preservatives, co-solvents, diluents, and the like.

The components of the synergistic antimicrobial combination of the present invention may be added to an article or system to be treated as separate entities, or as a combination. The two components are physically and chemically compatible and may be combined simply as active ingredients, or may additionally be combined with commonly employed carriers and excipients, as described above.

The 2-bromo-2-bromomethylglutaronitrile component of the synergistic antimicrobial combination of the present invention may be prepared in accordance with the procedures described in U.S. Pat. Nos. 3,833,731 and 3,873,597 referred to above. The 1,2-benzisothiazolin-3-one of Formula II may be prepared in accordance with procedures well known in the art.

The following examples, which were actually carried out, will serve to further illustrate the present invention, without at the same time, however, constituting any limitation thereof.

EXAMPLE 1

Clay Slurry Preservation

A. Individual Effective Concentration.

The individual effective concentrations of 2-bromo-2-bromomethylglutaronitrile (2-Br-2-BG) and 1,2-benzisothiazolin-3-one (1,2-BI-3-O) alone (75 ppm and 100 ppm, respectively), as well as their combination (50 ppm plus 25 ppm, respectively) were determined by addition of a ladder series of each biocide in a 14 day preservation test. A series of 100 gram aliquots of 70% Georgia Kaolin KCS clay slurry was used. The dosages in parts per million (ppm) were based on the total weight of slurry, and for the 2-Br-2-BG compound were for 100% active ingredient, while for the 1,2-BI-3-O compound the dosages were for a composition containing 30% active ingredient. At the initiation of the test, the zero time bacterial population was determined on the untreated control aliquot. Bacterial plate counts were performed on all test aliquots after 24 hours, 7 days, and 14 days using the standard bacterial serial dilution method. The microorganisms employed in the test were *Escherichia coli*, *Aerobacter aerogenes*, and *Pseudomonas aeruginosa*. The results are illustrated in Table I below.

TABLE 1

DETERMINATION OF EFFECTIVE CONCENTRATIONS OF INDIVIDUAL BIOCIDES IN CLAY SLURRY SYSTEMS

| Treatment | Microorganism Counts | | | |
|---|---|---|---|---|
| | 0 Time | 24 Hrs. | 7 Days | 14 Days |
| 25 ppm 1,2-BI—3-O | — | $2.1 \times 10^5$ | $4.3 \times 10^4$ | $1.8 \times 10^4$ |
| 50 ppm 1,2-BI—3-O | — | $3.8 \times 10^4$ | $4.1 \times 10^4$ | $4.3 \times 10^3$ |
| 75 ppm 1,2-BI—3-O | — | $1.5 \times 10^4$ | $1.2 \times 10^4$ | $5.6 \times 10^3$ |
| 100 ppm 1,2-BI—3-O | — | $2.4 \times 10^3$ | $1.8 \times 10^3$ | $6.7 \times 10^2$ |
| 150 ppm 1,2-BI—3-O | — | $4.2 \times 10^2$ | $6.2 \times 10^2$ | $1 \times 10^3$ |
| 50 ppm 2-Br—2-BG | — | $1.8 \times 10^4$ | $4.5 \times 10^4$ | $5.4 \times 10^4$ |
| 75 ppm 2-Br—2-BG | — | $6.9 \times 10^3$ | $1.8 \times 10^4$ | $4.2 \times 10^3$ |
| 100 ppm 2-Br—2-BG | — | $1.9 \times 10^2$ | $3.8 \times 10^2$ | $5 \times 10^3$ |
| 150 ppm 2-Br—2-BG | — | <100 | <100 | <100 |
| 200 ppm 2-Br—2-BG | — | <100 | <100 | <100 |
| Untreated Control | $6.8 \times 10^6$ | $1 \times 10^7$ | $3 \times 10^6$ | $1 \times 10^7$ |

B. Potentiation.

The potentiation activity of the combination of 2-Br-2-BG and 1,2-BI-3-O was determined by individual addition of each of the active ingredients to the clay slurry at concentrations that were inadequate to preserve the system alone. A series of 100 gram aliquots of Georgia Kaolin KCS clay slurry was used. The preservatives were added to the slurry separately, and were thoroughly mixed in before the addition of the co-preservative. During the treatments, the test aliquots were observed for any signs of reaction and incompatibility. At the initiation of the test, the zero time bacterial population was determined in the untreated control aliquot. Bacterial plate counts were performed on all test aliquots after 24 hours; 7 days; 2, 4, 6, and 8 weeks, using the standard bacterial serial dilution method. The microorganisms employed in the test were *Escherichia coli*, *Aerobacter aerogenes*, and *Pseudomonas aeruginosa*. The results are illustrated in Table II below.

TABLE II

DETERMINATION OF POTENTIATION EFFECTS OF BIOCIDE COMBINATION IN CLAY SLURRY SYSTEM

| Treatment | 0 Time | 24 Hrs. | 7 Days | 14 Days | 4 Weeks | 6 Weeks | 8 Weeks |
|---|---|---|---|---|---|---|---|
| 10 ppm 1,2-BI—3-O + 25 ppm 2-Br—2-BG | — | $2.6 \times 10^5$ | $4 \times 10^3$ | $4.4 \times 10^4$ | $6.2 \times 10^4$ | $3 \times 10^4$ | $5.2 \times 10^4$ |
| 25 ppm 1,2-BI—3-O + 25 ppm 2-Br—2-BG | — | $8.1 \times 10^4$ | $5.3 \times 10^4$ | $5.2 \times 10^4$ | $1.1 \times 10^5$ | $9.6 \times 10^4$ | $2.6 \times 10^4$ |
| 25 ppm 1,2-BI—3-O + 50 ppm 2-Br—2-BG | — | $1.8 \times 10^4$ | $2.3 \times 10^2$ | $3.8 \times 10^3$ | $1.2 \times 10^4$ | $4.8 \times 10^3$ | $3.2 \times 10^4$ |
| Untreated Control | $6.4 \times 10^6$ | $6.1 \times 10^6$ | $1.7 \times 10^6$ | $2.2 \times 10^6$ | $1.2 \times 10^7$ | $9.1 \times 10^6$ | $1.3 \times 10^5$ |

EXAMPLE 2

Metalworking Fluid Preservation

Petroleum base soluble and synthetic metalworking fluids were diluted 1:40 with water. A concentration of 500 ppm of 1,2-benzisothiazolin-3-one (1,2-BI-3-O) as a 30% active formulation was added to the individual test systems. There was then incorporated into each fluid 500 ppm of 2-bromo-2-bromomethylglutaronitrile (2-Br-2-BG) as a 100% active formulation. The biocides were evaluated alone and in combination. Inoculations of bacteria, yeast and fungi were made weekly and the microbiological population was analyzed once per week until failures were observed. A failure consisted of two consecutive weekly microbial counts of $10^5$ organisms/ml. The following Table III shows the number of days of inhibition provided by the biocides alone and in combination.

TABLE III

| Treatment | Days of Inhibition | |
|---|---|---|
| | Soluble Fluid | Synthetic Fluid |
| Untreated control | 0 | 0 |
| 500 ppm 2-Br—2-BG | 14 | 35 |
| 500 ppm 1,2-BI—3-O | 0 | 21 |
| 1000 ppm 2-Br—2-BG | 56 | 63 |
| 1000 ppm 1,2-BI—3-O | 7 | 42 |
| 500 ppm 2-Br—2-BG + 500 ppm 1,2-BI—3-O | 105* | 84 |

*Still inhibitory when taken off test.

What is claimed is:

1. A synergistic antimicrobial combination comprising:
   (a) 2-bromo-2-bromomethylglutaronitrile and
   (b) 1,2-benziothiazoline-3-one
   wherein for every 10 to 1000 parts of 2-bromo-2-bromomethylgutaronitrile there is from 3 to 300 parts of 1,2-benziothiazoline-3-one: and the ratio of 2-bromo-2-bromomethylglutaronitrile to 1,2-benziothiazoline-3-one is 6.7:1 to 1:3.

2. An antimicrobial composition comprising a carrier and an antimicrobially effective amount of a synergistic antimicrobial combination comprising:
   (a) 2-bromo-2-bromomethylglutaronitrile and
   (b) 1,2-benzisothiazoline-3-one
   wherein for every 10 to 1000 parts of 2-bromo-2-bromomethylglutaronitrile there is from 3 to 300 parts of 1,2-benzisothiazoline-3-one; and the ratio of 2-bromo-2-bromomethylglutaronitrile to 1,2-benzisothiazoline-3-one is 6.7:1 to 1:3.

3. A method of inhibiting microbial growth which comprises contacting microorganisms with an antimicrobially effective amount of a synergistic antimicrobial combination comprising:
   (a) 2-bromo-2-bromomethylglutaronitrile and
   (b) 1,2-benzisothiazoline-3-one of the;
   wherein for every 10 to 1000 parts 2-bromo-2-bromomethylglutaronitrile there is from 3 to 300 parts of 1,2-benzisothiazoline-3-one; and the ratio bf 2-bromo-2-bromomethylglutaronitrile to 1,2-benzisothiazoline-3-one is 6.7:1 to 1:3.

4. A method according to claim 3 wherein the components of the combination are applied together as a single composition.

5. A method according to claim 3 wherein the components of the combination are applied separately.

6. A method of inhibiting the growth of bacteria and fungi in latex paints and latex emulsions and adhesives comprising incorporating into said latex paints, emulsions, and adhesives so as to contact said bacteria and fungi, at least a bactericidally and fungicidally effective amount of a synergistic antimicrobial combination comprising:
   (a) 2-bromo-2-bromomethylglutaronitrile
   (b) 1,2-benzisothiazoline-3-one
   wherein 2-bromo-2-bromomethylglutaronitrile is employed in an amount to provide a concentration between 100 and 1000 ppm and 1,2-benzisothiazoline-3-one is employed in an amount of provide a concentration between 150 and 300 ppm; and the ratio of 2-bromo-2-bromomethylglutaronitrile to 1,2-benzisothiazoline-3-one is 6.7:1 to 1:3.

7. A method according to claim 6 wherein the components of the combination are applied together as a single composition.

8. A method according to claim 6 wherein the components fo the combination are applied separately.

9. A method of inhibiting the growth of bacteria and fungi in metalworking fluids comprising incorporating into said fluids so as to contact said bacteria and fungi, at least a bactericidally and fungicidally effective amount of a synergistic antimicrobial combiantion comprising:
   (a) 2-bromo-2-bromomethylglutaronitrile and
   (b) 1,2-benzisothiazoline-3-one
   wherein 2-bromo-2bromomethylglutaronitrile is employed in an amount to provide a concentration between 100 and 1000 ppm and 1,2-benzisothiazoline-3-one is employed to provide a concentration between 150 and 300 ppm; and the ratio of 2-bromo-2-bromomethylgluatonitrile to 1,2-benzisothiazoline-3-one is 6.7 to 1:3.

10. A method according to claim 9 wherein the components of the combination are applied together as a single composition.

11. A method according to claim 9 wherein the components of the configuration are applied separately.

12. The synergistic antimicrobial combination of claim 1, wherein the ratio of 2-bromo-2-bromomethylglutaronitrile to 1,2-benzisothiazoline-3-one is 2.5:1 to 1:1.

13. The antimicrobial composition of claim 2, wherein the ratio of 2-bromo-2-bromomethylglutaronitrile to 1,2-benzisothiazoline-3-one is 2.5:1 to 1:1.

14. The method of claim 3, wherein the ratio of 2-bromo-2-bromomethylglutaronitrile to 1,2-benzisothiazoline-3-one is 2.5:1 to 1:1.

15. The method of claim 6, wherein the ratio of 2-bromo-2-bromomethylglutaronitrile to 1,2-benzisothiazoline-3-one is 2.5:1 to 1:1.

16. The method of claim 9, wherein the ratio of 2-bromo-2-bromomethylglutaronitrile to 1,2-benzisothiazoline-3-one is 2.5:1 to 1:1.

* * * * *